United States Patent [19]

Norberg et al.

[11] Patent Number: 5,162,471
[45] Date of Patent: Nov. 10, 1992

[54] CARBOHYDRATEACRYL- AND METHACRYLCOPOLYMERS AND THEIR MANUFACTURE

[75] Inventors: Thomas Norberg, Lund; Elisabeth Kallin, Södra Sanby, both of Sweden

[73] Assignee: BioCarb AB, Sweden

[21] Appl. No.: 601,733

[22] PCT Filed: Feb. 16, 1990

[86] PCT No.: PCT/SE90/00107
§ 371 Date: Oct. 31, 1990
§ 102(e) Date: Oct. 31, 1990

[87] PCT Pub. No.: WO90/10023
PCT Pub. Date: Sep. 7, 1990

[30] Foreign Application Priority Data
Mar. 1, 1989 [SE] Sweden .................. 8900605

[51] Int. Cl.$^5$ ............................... C08F 24/00
[52] U.S. Cl. .................... 526/266; 526/270; 526/304
[58] Field of Search .................. 526/266, 270, 304

[56] References Cited

FOREIGN PATENT DOCUMENTS 0126043 10/1989 European Pat. Off. .

OTHER PUBLICATIONS

K. Kobayashi et al. Polym. J. 15 (9), 667-671 (1983).
P. Kosma, G. Schulz, and F. M. Unger, Carbohydr. Res., 180, 19-28 (1988).
R. Roy and F. Tropper, Glycoconjugate J., 5., 203-206 (1988).
E. Kallin, H. Lönn, and T. Norberg, Glycoconjugate J., 5, 145-150 (1988).
E. Kallin, H. Lönn, and T. Norberg, Glycoconjugate J. 3, 311-319 (1986).
P. Kosma, J. Gass, G. Schulz, R. Christian, and F. M. Unger, Carbohydr Res., 167, 39-54 (1987).
R. Roy, C. A. Laferriére, A. Gamian, H. J. Jennings, J. Carbohydr. Chem., 6, 161-165 (1987).
H. Paulsen and K.-W. Pflughaupt in The Carbohydrates, vol. 1B, W. Pigman and D. Horton, Eds.; Academic Press: N. Y., 1980, pp. 881-927.
A. Ya. Chernyak, A. B. Levinsky, B. A. Dmitriev, and N. K. Kochetkov, Carbohydr. Res., 128, 269-282 (1984).
A. Ya. Chernyak, K. V. Antonov, N. K. Kochetkov, L. N. Padyukov, and N. V. Tsvetkova, Carbohydr. Res., 141, 199-212 (1985).

*Primary Examiner*—Joseph L. Schofer
*Assistant Examiner*—M. Nagumo
*Attorney, Agent, or Firm*—Burns, Doane, Swecker & Mathis

[57] ABSTRACT

A copolymer of an N-acylated glycosylamine and an amide having the general formula:

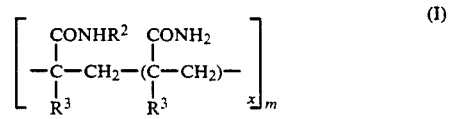

(I)

wherein
$R^2$ is a reducing sugar residue;
$R^3$ is H or $CH_3$;
x is an integer from 0 to about 20; and
m is such that the molecular weight of the copolymer is from about 5 kDa to about 2000 kDa;
an N-acryloyl- or methacryloyl-glycosylamine having the formula:

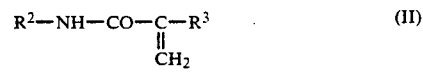

(II)

wherein
$R^2$ is a reducing sugar residue; and
$R^3$ is H or $CH_3$; and
processes for its preparation.

17 Claims, 2 Drawing Sheets

CARBOHYDRATEACRYL- AND METHACRYLCOPOLYMERS AND THEIR MANUFACTURE

The present invention relates to copolymers of glycosyl amines and amides, to N-acryloyl- or methacryloyl-glycosylamines and to processes for their preparation.

BACKGROUND OF THE INVENTION

Carbohydrate structures, exposed on the surface of cells or occurring in soluble form in body fluids, are important in many biological recognition processes. To investigate such processes, low molecular weight oligosaccharides are sometimes not satisfactory. Therefore, a great deal of effort has been devoted to the development of techniques (ref. 1 to 4) for attaching oligosaccharides to larger molecules such as proteins, to give high molecular weight, multivalent conjugates. The obtained "neoglycoproteins" can be used as immunizing antigens to produce carbohydrate-directed antibodies, or as antigens in immunoassays to detect such antibodies.

However, for many applications, it is problematic to use protein conjugates. For example, in immunoassays using carbohydrate antigens, the presence of protein epitopes is highly undesirable. An alternative to proteins in these cases are water-soluble, weakly immunoreactive polymers of the polyacrylamide type. Several reports have recently appeared describing the preparation of oligosaccharide-acrylamide copolymers, both linear (ref. 5 to 14) and crosslinked (ref. 15 to 17). The general strategy for preparation of these conjugates has been to attach an olefinic group to a carbohydrate, and then copolymerize this derivative with acrylamide. The olefinic group has been introduced into the carbohydrate molecule either as an allyl glycoside at an early stage in a synthetic scheme (ref. 5–7, 9–12 and 15), by acryloylation of an amino function of a mono- or oligosaccharide derivative (ref. 8, 11, 13, 14, 17), or by other methods (ref. 16). These known techniques are, however, subject to drawback in that they cannot be directly applied to reducing di- or oligosaccharide reactants, since the reaction conditions necessary result in cleavage of interglycosidic linkages.

Few reports have appeared to date (ref. 14, 18) on the attachment of an olefinic group onto a reducing oligosaccharide. Reducing oligosaccharides of great complexity and structural variety can be isolated from natural sources such as milk (ref. 19), urine (ref. 20), and faeces (ref. 20), and also from chemical or enzymatic hydrolyzates of glycoproteins (ref. 21), glycolipids (ref. 22, 23), or lipopolysaccharides (ref. 24).

SUMMARY OF THE INVENTION

The present invention is directed to new techniques for the attachment of an olefinic group to the anomeric position of reducing saccharides. Generally, the invention is based on conversion of the saccharides used into the corresponding β-glycosyl amines which are then N-acryloylated or N-methacryloylated. The N-acryloyl- or N-methacryloylglycosylamines formed are then copolymerized with acrylamide or methacrylamide to form high molecular weight, linear polymers. These new polymers are useful in for example applications involving coating antigens in ELISA assays.

According to a first aspect the invention thus provides for a copolymer of glycosyl amine and an amide, said copolymer having the general formula:

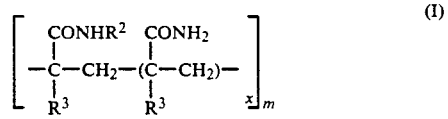

wherein
$R^2$ is a reducing sugar residue;
$R^3$ is H or $CH_3$;
x is an integer from 0 to about 20; and
m is such that the molecular weight of the copolymer is from about 5 kDa to about 2000 kDa.

It is preferred that $R^2$ in formula I above is a mono-, di- or oligo-saccharide residue. Particularly preferred are saccharides having 1 to 10 monosaccharide units, especially 1 to 6 units.

Although the invention is not to be construed to be limited thereto, examples of saccharides of which $R^2$ denotes the residue are: lactose, lacto-N-tetraose, lacto-N-fucopentaose I, lacto-N-fucopentaose II, lacto-N-difucohexaose I, 2'-fucosyllactose, 3'-siallyllactose, A-tetrasaccharide, cellobiose.

In formula I above x is preferably from 1 to about 15, and m is preferably such that the molecular weight of the copolymer is from about 10 to about 500 kDa. It is preferred that $R^3$ of formula I is hydrogen corresponding to using acrylamide as one repeating entity in the copolymer I.

In the above formula I symbol m is defined by functional statement on molecular weight of the copolymer. Generally, the molecular weight range 5 to 2000 kDa as given above corresponds to an approximate range for symbol m of from about 5 to about 3000, such as from about 50 to about 750. The fact that these ranges are of an approximative nature is, of course, due to the fact that the other variables of formula I, i.e. $R^2$, $R^3$ and x, result in varying molecular weights for the entity within the main bracket of the formula.

According to another aspect the invention provides for new N-acryloyl- or methacryloyl-glycosylamines having the formula:

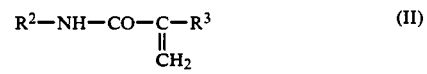

wherein
$R^2$ is a reducing sugar residue; and
$R^3$ is H or $CH_3$.
In this formula II $R^2$ and $R^3$ have the meanings defined in relation to general formula I above.

According to a further aspect the invention provides for a process for preparing an N-acryloyl- or methacryloyl-glycosylamine having the formula:

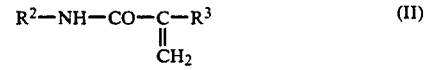

wherein
$R^2$ is a reducing sugar residue; and
$R^3$ is H or $CH_3$, comprising the steps:

a) reacting a reducing sugar in solution and ammonium hydrogen carbonate to form an N-acryloyl glycosylamine;

b) reacting the glycosylamine obtained in step a) with a reactive derivative of acrylic or methacrylic acid; and c) recovering the resulting N-acryloyl glycosylamine.

It is preferred to use a halide or anhydride in step b) above, and especially preferred is the use of acryloyl chloride in said step.

According to yet another aspect the invention provides for a process for preparing copolymers having the general formula I as defined above, said process comprising the steps:

a) polymerizing in solution an N-acryloyl- or N-methacryloyl glycosylamine and acrylamide or methacrylamide; and b) recovering the resulting copolymer.

In this process the amide is preferably used in stoichiometric excess, and the use of acrylamide in step a) is particularly preferred.

As previously indicated the copolymers of the present invention are useful in a variety of applications, of which some are exemplified below.

As a first example of practical use of the present invention there may be mentioned the copolymer based on the N-acryloyl or -methacryloyl glycosylamine of lacto-N-tetraose ($\beta$-D-Galp-(1->3)-$\beta$-D-GlcNAcp-(1->3)-$\beta$-D-Galp-(1->4)-D-Glc), and acrylamide, said copolymer being further described below in the exemplifying section of the specification. This copolymer is useful in its capacity of acting as a bacterial receptor enabling diagnosing and inhibiting bacterial adherence of for example pneumococci as disclosed in published European patent application 84850084.9. The disclosure of said European application is enclosed herein by reference.

Another example of practical application of the invention is the use of the corresponding copolymer based on the so called A-tetrasaccharide ($\alpha$-D-GalNAcp-(1->3)-[$\alpha$-L-Fucp-(1->2)]-$\beta$-D-Galp-(1->4)-$\beta$-D-Glc) in that the copolymer shows excellent binding to anti-A and is thus useful in blood-testing using for example copolymer-coating in ELISA-assays.

A third example of practical application relates to the corresponding copolymer based on lacto-N-fucopentaose ($\alpha$-L-Fucp-(1->2)-$\beta$-D-Galp-(1->3)-$\beta$-D-GlcNAcp-(1->3)-$\beta$-D-Galp-(1->4)D-Glc), said copolymer being useful in the control of uterine implantation of embryos in mammals. This application is in accordance with published European patent application No. 88850221.8, the full disclosure being incorporated herein by reference. The usefulness of the copolymer based on this carbohydrate is emphasized by the fact that an amplified effect in the control of uterine implantation is obtained due to the multivalent character of the copolymer.

The present invention will now be further described by nonlimiting examples with reference to the appended drawings, wherein.

EXAMPLES

General procedures

Figure 1:
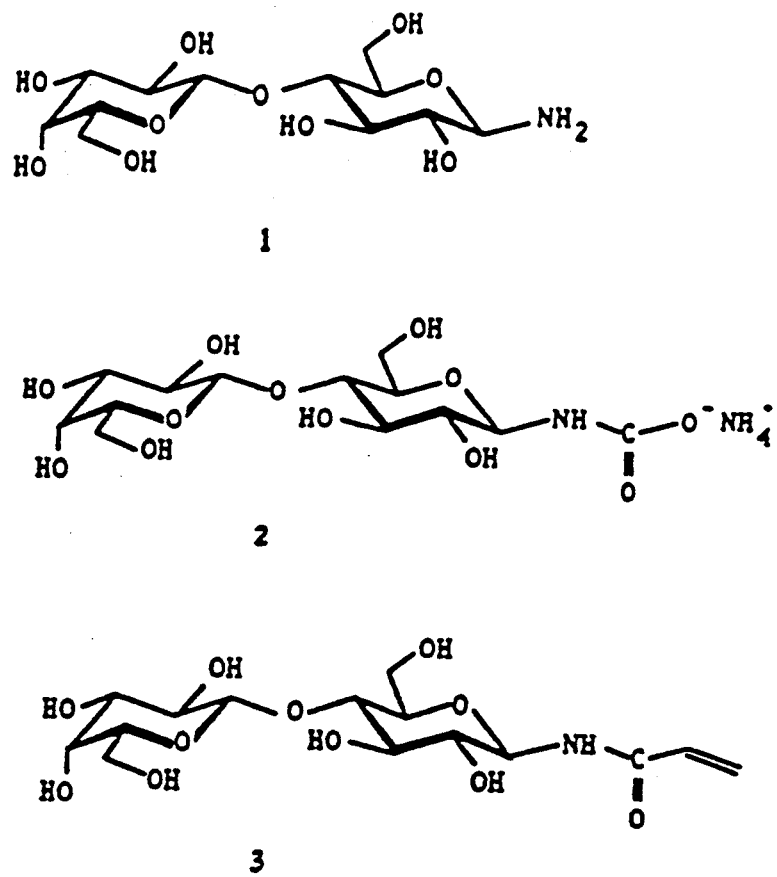
FIG. 1 illustrates the process steps involved in the manufacture of the copolymer.

Pure oligosaccharides, isolated from human milk (ref. 19), urine (ref. 20) or other sources were treated with aqueous ammonium bicarbonate, essentially as previously described (ref. 26), to give the corresponding glycosylamines (FIG. 1). The yields were as reported in Table 1. In all cases where oligosaccharides terminating with 4-linked glucose were used, $\beta$-pyranosidic glycosylamines were the main product. Less than 5% of the bis-$\beta$-glycosylamine (ref. 27, 28) was detected (NMR, H-1 at $\delta$ 4.32). No $\alpha$-anomeric product signals were detected in any of the NMR spectra.

Figure 2:
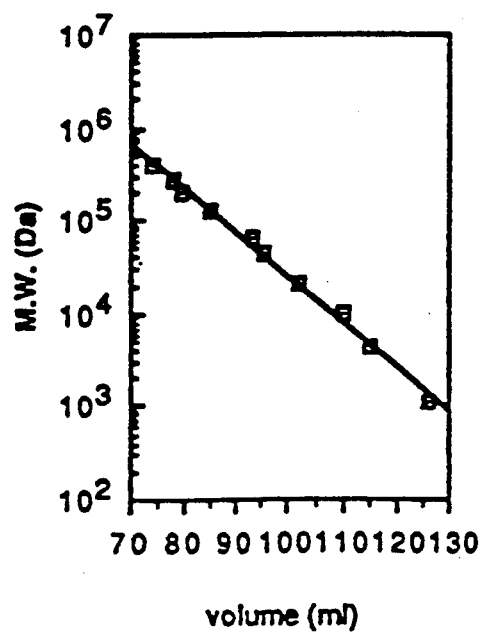
FIG. 2 illustrates NMR spectra on reactions between lactose and ammoniumhydrogen carbonate.
Figure 3:
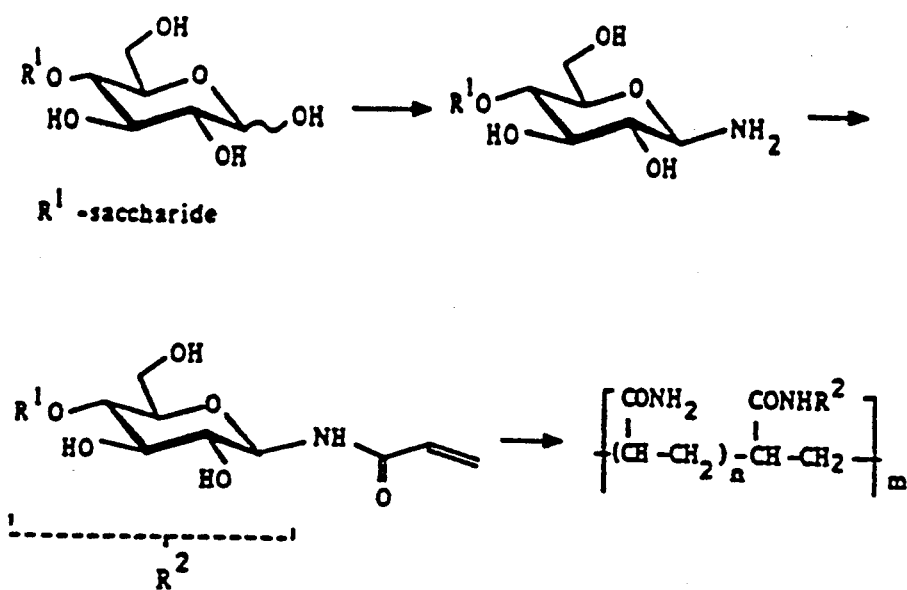
FIG. 3 illustrates three different intermediates in such manufacturing process.

For closer inspection of the reaction path leading to the glycosylamines, the reaction between lactose and ammonium bicarbonate was performed in D$_2$O and monitored by $^1$H NMR spectroscopy. It was shown (FIG. 2) that after 24 h at room temperature, about 50% of the lactose had been converted. After 5 days, more than 95% of the starting material had disappeared. However, only minor amounts of the glycosylamine 1 (H-1 at $\delta$ 4.12, H-2 at $\delta$ 3.20) were detected. Instead, signals from another major product (H-1 at $\delta$ 4.70, H-2 at $\delta$ 3.38) were present (see FIG. 3). This product was assumed to be the N-glycosylcarbamate 2. Signals from another, unidentified minor product (H-1 at $\delta$ 6.29, H-2 at $\delta$ 4.71) were also present. That 2 was indeed present in the reaction mixture was also indicated by a FAB-MS spectrum of the mixture, where peaks corresponding to the acid of 2 (m/z 386) and 2 (m/z 403) were detected. After processing of the reaction mixture by evaporation, adsorption to a cation exchange column, elution with methanolic ammonia and evaporation, the $^1$H NMR spectrum of a D$_2$O solution showed presence of pure 1 (H-1 at $\delta$ 4.12), the yield was 82%. Therefore, any N-glycosylcarbamate (2) present in the reaction mixture must have decomposed into the glycosylamine (1) during processing, an expected reaction for this type of derivative (ref. 29). The importance of 2 as an intermediate was indicated by the fact, that reaction of lactose with concentrated aqueous solutions of ammonium acetate, ammonium formiate, or ammonium chloride gave less than 10% conversion (TLC evidence) after 5 days at room temperature.

The influence of pH on the stability of glycosylamine solutions was also investigated. Lactose glycosylamine (1) was dissolved in phosphate buffers of different pH and the solutions were monitored polarimetrically. Solutions in the pH range 8.0–10.0 were found to undergo little change during several days at room temperature. This was also confirmed by the observation, that the $^1$H NMR spectrum of 1 in D$_2$O (10 mg/mL, pH 7.7) did not change during this period. Lowering the pH increased the rate of decomposition of 1. At pH 5, for example, 1 was completely converted to lactose in less than 1 hour. However, at low pH (0.5M aqueous HCl) 1 was again stable. These results are in good agreement with those reported for similar glycosylamines (ref. 30). However, we also noted a lower stability of glycosylamines in borate buffers. At pH 10.0 in 0.1M borate buffer, lactose glycosylamine was converted to lactose in less than 5 min (optical rotation and TLC evidence). The reason for this needs to be investigated.

On basis of the above stability investigations, it was concluded that N-acylation of the glycosylamines in hydroxylic solvents should be possible, provided that the acylation reaction is fast and selective for amino groups, and that the pH during the reaction can be kept above 8. Indeed, several acylating agents were successfully used, and this communication reports on the results with acryloyl chloride. Treatment of the glycosylamines in Table 2 with acryloyl chloride in aqueous methanol using sodium carbonate as buffer gave satisfactory yields of the corresponding N-acryloyl glycosylamines (FIG. 1, Table 2). The N-acryloyl glycosylamines were, as predicted (ref. 30), much more stable towards hydrolysis than the glycosylamines. However, the presence of the acryloyl group introduced a marked tendency to self-polymerization (ref. 13, 14), therefore addition of small amounts of a radical inhibitor to the solutions of these compounds was necessary during some operations.

Radical copolymerization of the oligosaccharide N-acryloyl glycosylamines with acrylamide in aqueous solution using ammonium persulfate/tetramethylethylenediamine (TEMED) as initiator system (ref. 5) gave linear polymers (FIG. 1, Table 3). The carbohydrate contents of the polymers were determined by integration of appropriate signals in the $^1$H NMR spectra, and also independently by the anthrone-sulfuric acid colorimetric method (ref. 31). The yield of carbohydrate incorporated into the polymer varied from 48 to 82%. The molar ratio oligosaccharide groups/CH-CH$_2$ groups in the polymer agreed well with the corresponding ratio in the pre-polymerization mixture (Table 3). This is in contrast to what is the case (ref. 6, 9, 12) when allyl glycosides are copolymerized with acrylamide. Here lower yields are obtained and much lower oligosaccharide/CH-CH$_2$ ratios are found in the polymer than in the reaction mixture, since the reactivity of allyl glycosides in radical reactions is lower than that of acrylamide. Obviously, N-acryloyl sugar derivatives have a higher reactivity (ref. 11) in this respect.

Figure 4:
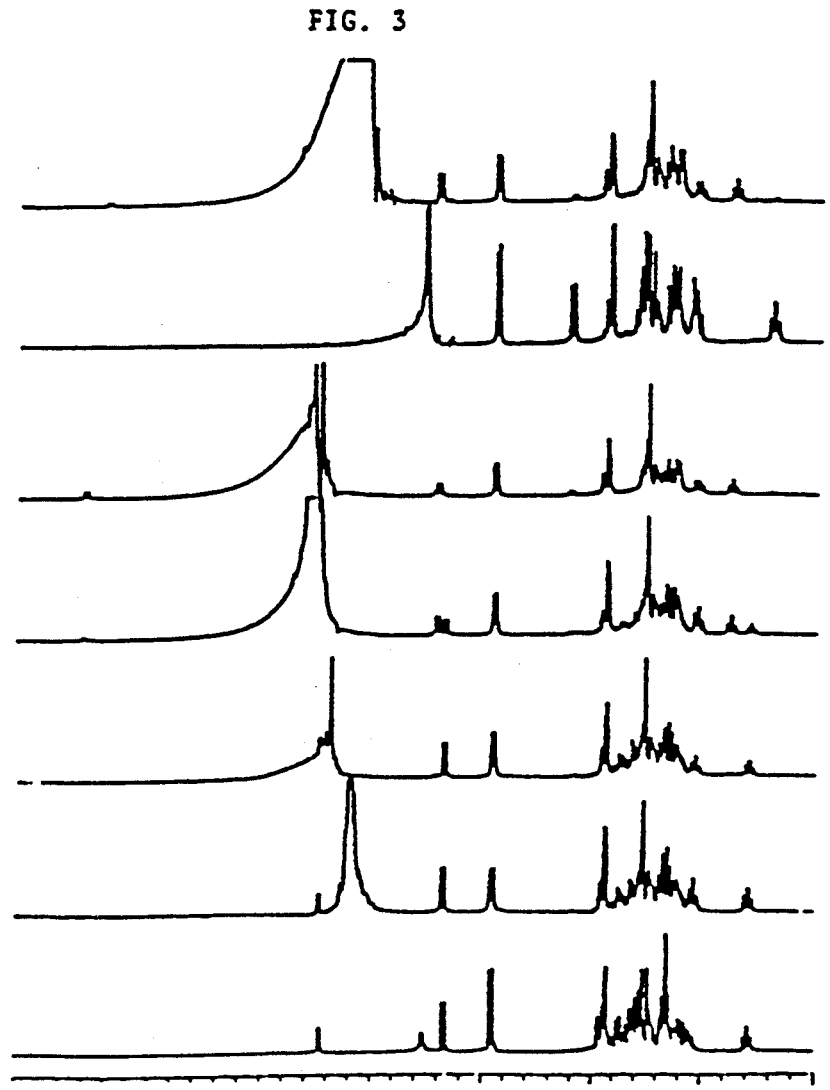
FIG. 4 is a diagram showing the average molecular weight of the copolymers versus gel filtration elution volume.

The average molecular weights of the polymers (usually in the range of 100–500 kDa) were determined from the gel filtration elution volume using dextran standards for calibration (FIG. 4). The molecular weights so determined agreed well with those determined by ultrafiltration through filters with different pore sizes.

In order to find optimal conditions for obtaining a high molecular weight polymer, several sets of experiments were performed with the N-acryloyl derivative of lactose. It was found that, as expected (ref. 32–34), the molecular weight increased with decreasing concentration of ammonium persulfate and increasing concentration of monomers. However, too high a concentration of monomer resulted in an insoluble product. The reaction temperature is expected (ref. 32–33) to affect polymer molecular weight, but the effect was found to be moderate when varying between 0° and 20° C. We also found little effect of pH (5 and 9) of the reaction mixture on the molecular weight distribution of the polymer, and there was no detectable change when the acrylamide to sugar monomer ratio was changed from 10:1 to 2:1. Factors that were found to be important for a good result were the purity of the monomers and an oxygen-free reaction mixture (ref. 7). Factors that were not investigated but are known (ref. 32–34) to affect polymer molecular weight are initiator type and presence of chain transfer agents such as salts or alcohols.

The obtained copolymers exhibited strong specific binding to antibodies against the carbohydrate portion when used as coating antigens in ELISA assays. Thus, as reported before (ref. 6, 11), carbohydrate-acrylamide copolymers are alternatives to glycolipid or glycoprotein antigens in immunological assays. Other biological properties of carbohydrate-acrylamide copolymers, such as the ability to inhibit or promote various biological processes are being investigated in this laboratory.

Degassed distilled water was used. All reactions except the preparation of glycosylamines were performed under nitrogen. Concentrations were performed at <30° C. (bath). Optical rotations were recorded at 21° C. with a Perkin-Elmer 241 polarimeter. NMR spectra were recorded at 27° C. in D$_2$O with a Bruker AM 500 instrument, using acetone methyl signals ($\delta_H$ 2.225 and $\delta_C$ 23.2) as internal standards. The FAB-MS spectra were recorded with a VG ZAB-SE mass spectrometer. The primary beam consisted of xenon atoms with a maximum energy of 8 keV. The samples were dissolved in thioglycerol and the positive ions were extracted and accelerated over a potential of 10 kV. Thin layer chromatography was performed on silica gel 60 F$_{254}$ (Merck, Darmstadt, FRG) using 4:3:3:2 ethyl acetate:acetic acid:methanol:water as eluant. The spots were visualized by charring with 5% sulfuric acid. Acrylamide (enzyme grade, Eastman Kodak C:o, Rochester, N.Y., USA) was used without further purification. Bond-Elut C-18 and SCX cartridges and Sepralyte C18 silica gel were from Analytichem International (Harbor City, USA). Bio-Gel P2 (Bio-Rad, Richmond, USA) and Fractogel TSK HW55 (F) (Merck, Darmstadt, FRG) columns were packed and eluted with water. Dextran standards were from Pharmacosmos (Viby, Denmark). Ultrafiltration equipment (Omega cells) were from Filtron AB (Bjärred, Sweden). The tetrahydrofuran (Riedel-de Haen, FRG) used contained 250 mg/L of 2,6-di-tert-butyl-4-methylphenol as stabilizing agent.

EXAMPLE 1

Preparation of Glycosylamines:

Solid ammonium bicarbonate was added until saturation to a solution of oligosaccharide (50 mg) in water (2.5 mL). The mixture was stirred in an open vessel at room temperature for 3–7 days. Ammonium bicarbonate was added at intervals, saturation was assured by always keeping a portion of solid salt present in the mixture. When TLC indicated no more conversion, the mixture was diluted with water (5 mL) and concentrated to half the original volume. The residue was diluted to 20 mL with water and concentrated to 5 mL. This process was repeated once, then the residue was diluted to 10 mL and lyophilized. The crude product was purified by dissolving in water (1 mL) and passing the solution through a cation exchange resin (Bond-Elut SCX, H$^+$-form, 0.5 g cartridge). After washing the resin with water, the glycosylamine was eluted with 2M ammonia in 1:1 methanol-water (2.5 mL). The eluate was concentrated to 1 mL and then lyophilized.

4-0-($\beta$-D-Galactopyranosyl)-$\beta$-D-glucopyranosylamine (1).

Treatment of lactose (50 mg) as described above gave 1 (41 mg, 82%), $[\alpha]_D$ +37° (c 1.0 water), lit. (ref. 35) $[\alpha]_D$ +38.5 (water).

NMR data: $^{13}C$, δ61.1 (C-6), 61.9 (C-6'), 69.4 (C-4'), 71.8 (C-2'), 73.4 (C-3'), 74.8 (C-2), 76.0 (C-3), 76.2 (C-5'), 76.5 (C-5), 79.5 (C-4), 85.7 (C-1), 103.7 (C-1'); $^1H$, δ3.20 (dd, $J_{1,2}$ 8.7, $J_{2,3}$ 9.4 Hz, H-2), 3.54 (dd, $J_{1',2'}$ 7.8, $J_{2',3'}$ 9.9 Hz, H-2'), 3.55 (ddd, $J_{4,5}$ 9.6, $J_{5,6a}$ 5.0, $J_{5,6b}$ 2.3 Hz, H-5), 3.62 (dd, $J_{2,3}$ 9.4, $J_{3,4}$ 8.7 Hz, H-3), 3.64 (dd, $J_{3,4}$ 8.7, $J_{4,5}$ 9.6 Hz, H-4), 3.66 (dd, $J_{2',3'}$ 9.9, $J_{3',4'}$ 3.4 Hz, H-3'), 3.72 (ddd, $J_{4',5'}$ 1.1, $J_{5',6'a}$ 3.8, $J_{5',6'b}$ 8.1 Hz, H-5'), 3.75 (dd, $J_{5',6'a}$ 3.8, $J_{6a,6b}$ 11.6 Hz, H6a), 3.78 (dd, $J_{5,6a}$ 5.0, $J_{6a,6b}$ 12.1 Hz, H6a), 3.79 (dd, $J_{5',6'b}$ 8.1, $J_{6'a,6'b}$ 11.6 Hz, H-6'b), 3.92 (dd, $J_{3',4'}$ 3.4, $J_{4',5'}$ 1.1 Hz, H-4'), 3.94 (dd, $J_{5,6b}$ 2.3, $J_{6a,6b}$ 12.1 Hz, H-6b), 4.11 (d, $J_{1,2}$ 8.7 Hz, H-1), 4.45 (d, $J_{1',2'}$ 7.8 Hz, H-1').

Anal. Calcd. for $C_{12}H_{23}NO_{10} \times H_2O$: C, 40.1; H, 7.0; N, 3.9. Found: C, 40.3; H, 6.8; N, 3.8. A FAB-MS spectrum showed an M+1 ion at m/z 342.

EXAMPLE 2

N-Acryloylation of Glycosylamines

Sodium carbonate (100 mg) and methanol (1.0 mL) was added to a solution of the glycosylamine (0.14 mmol) in water (1.0 mL). The mixture was stirred at 0° C. while acryloyl chloride (60 μL, 0.74 mmol) in tetrahydrofuran (0.5 mL) was added during 5 min. After 10 min, the solution was diluted with water (3 mL) and concentrated to 2 mL. The solution was again diluted with water (2 mL), 200 μL of 0.5% 2,6-di-tert-butyl-4-methylphenol in tetrahydrofuran (inhibitor solution) was added, and the solution was concentrated to 1-2 mL. This solution was applied onto a C-18 silica gel column (2.0×5.0 cm), packed in water. Elution with water gave salts, unreacted glycosylamine, and reducing sugar in the first fractions, and the desired product in the later fractions. In some cases, elution of the product was preferably speeded up by adding methanol to the eluant. The fractions containing product were pooled, mixed with a few drops of inhibitor solution, and concentrated to 2 mL. This solution was purified by gel filtration on a Bio-Gel P2 column. Appropriate fractions were pooled and lyophilized.

N-Acryloyl-4-0-(β-D-galactopyranosyl)-β-D-glucopyranosylamine (3)

Treatment of 1 (50 mg) with acryloyl chloride (60 mL) as described above gave 3 (51 mg, 88%), $[\alpha]_D$ −7° (c 0.5, water). NMR data: $^{13}C$, δ60.7 (C-6), 61.9 (C-6'), 69.4 (C-4'), 71.8 (C-2'), 72.3 (C-2), 73.3 (C-3'), 75.9 (C-3), 76.2 (C-5'), 77.3 (C-5), 78.6 (C-4), 80.1 (C-1), 103.7 (C-1'), 130.20, 130.25 (CH=CH$_2$), 170.2 (C=O); $^1H$, δ3.49 (dd, $J_{1,2}$ 9.2, $J_{2,3}$ 9.2 Hz, H-2), 3.56 (dd, $J_{1',2'}$ 7.8, $J_{2',3'}$ 9.9 Hz, H-2'), 3.67 (dd, $J_{2'3'}$ 9.9, $J_{3',4'}$ 3.4 Hz, H-3'), 3.70 (m, H-5), 3.72 (m, H-3), 3.73 (m, H-4), 3.75 (m, H-5'), 3.77 (dd, $J_{5',6'b}$ 3.8, $J_{6'a,6'b}$ 11.6 Hz, H-6'b), 3.80 (dd, $J_{5',6'a}$ 8.2, $J_{6'a,6'b}$ 11.6 Hz, H-6'a), 3.82 (dd, $J_{5,6b}$ 4.4, $J_{6a,6b}$ 12.3 Hz, H-6b), 3.93 (dd, $J_{3',4'}$ 3.4, $J_{4',5'}$ 1.6 Hz, H-4'), 3.94 (dd, $J_{5,6a}$ 2.1, $J_{6a,6b}$ 12.3 Hz, H-6a), 4.46 (d, $J_{1',2'}$ 7.8 Hz, H-1'), 5.08 (d, $J_{1,2}$ 9.2 Hz, H-1), 5.87 (dd, J 3.7 and 7.9 Hz, CH=CH$_2$), 6.31 (m, CH=CH$_2$).

Anal. Calcd. for $C_{15}H_{25}NO_{11}$: C, 45.6; H, 6.4; N, 3.5. Found: C, 41.1; H, 6.1; N, 3.6.

EXAMPLE 3

Copolymerization of N-Acryloylglycosylamines with Acrylamide:

A solution of the N-acryloylglycosylamine (52 μmol) and acrylamide (210 μmol, 15 mg) in distilled water (400 μL) was deaerated by flushing with nitrogen for 20 min. The solution was then stirred at 0° C. and N,N,N',N'-tetramethylethylenediamine (2 μL) and ammonium persulfate (1 mg) were added. The mixture was slowly stirred at 0° C. for 2 h, and then at room temperature overnight. The viscous solution was diluted with water (1 mL) and purified by gel filtration on Fractogel HW 55(F). Fractions containing polymer were pooled and lyophilized.

Copolymer of N-Acryloyl-4-0-(β-D-galactopyranosyl)-β-D-glucopyranosylamine and acrylamide:

Treatment of 3 (20 mg) with acrylamide (7.2 mg, 2 eq) as described above gave copolymer (18 mg, 54% calculated from 3), $[\alpha]_D$ +7° (c 0.1, water). Analysis of the material by $^1H$ NMR spectroscopy (D$_2$O, 50° C.) showed presence of approximately 1 lactose unit per 4.6 CHCH$_2$ units (theoretical value: ⅕). The molecular weight distribution of the copolymer, as determined by gel filtration, was 50-1000 kDa, centered around 300 kDa.

REFERENCES

1. E. Kallin, H. Lönn, and T. Norberg, Glycoconjugate J., 3, 311-319 (1986).
2. C. P. Stowell and Y. C. Lee, Adv. Carbohydr. Chem. Biochem., 37, 225-281.
3. J. D. Aplin and J. C. Wriston, Jr, C.R.C. Crit. Rev. Biochem., 259-306 (1981).
4. Y. C. Lee and R. T. Lee in The Glycoconjugates, Vol IV; M. I. Horowitz, Ed.; Academic press: New York, 1982, p 57-83.
5. V. Horejsí, P. Smolek, and J. Kocourek, Biochem. Biophys. Acta, 538, 293-298 (1978).
6. A. Ya. Chernyak, K. V. Antonov, N. K. Kochetkov, L. N. Padyukov, and N. V. Tsvetkova, Carbohydr. Res., 141, 199-212 (1985).
7. A. Ya. Chernyak, A. B. Levinsky, B. A. Dmitriev, and N. K. Kochetkov, Carbohydr. Res., 128, 269-282 (1984).
8. A. Ya. Khorlin and N. V. Bovin, Bioorg. Chem., 11, 671-673 (1985).
9. P. Kosma, J. Gass, G. Schulz, R. Christian, and F. M. Unger, Carbohydr. Res., 167, 39-54 (1987).
10. P. Kosma, G. Schulz, and F. M. Unger, Carbohydr. Res., 180, 19-28 (1988).
11. R. Roy and F. Tropper, Glycoconjugate J., 5, 203-206 (1988).
12. R. Roy, C. A. Laferrière, A. Gamian, H. J. Jennings, J. Carbohydr. Chem., 6, 161-165 (1987).
13. R. L. Whistler, H. P. Panzer, and H. J. Roberts, J. Org. Chem., 26, 1583-1588 (1961).
14. J. Klein and D. Herzog, Macromol, Chem., 188, 1217-1233 (1987).
15. V. Horejsi and J. Kocourek, Biochem. Biophys. Acta, 297, 346-351 (1973).
16. R. T. Lee, S. Cascio, and Y. C. Lee, Anal. Biochem., 95, 260-269 (1979).
17. P. H. Weigel, R. L. Schnaar, S. Roseman, and Y. C. Lee in Methods in Enzymology, Vol 83, V. Ginsburg, Ed.; Academic press: Orlando, 1982, p 294-299.
18. K. Kobayashi, H. Sumitomo, and Y. Ina, Polymer J., 15, 667-671 (1983).
19. A. Kobata in Methods in Enzymology, Vol 28, V. Ginsburg, Ed.; Academic Press: Orlando, 1973, p 262-271.

20. A Lundblad and A. Chester in The Molecular Immunology of Complex Carbohydrates, A. Wu, Ed.; Plenum Press: New York, 1988.
21. A. Kobata In Biology of Carbohydrates, Vol 2; V. Ginsburg and P. W. Robbins, Eds.; John Wiley: New York, 1984, p 87-161.
22. H. Wiegandt and H. Bücking, Eur. J. Biochem., 15, 287-292. (1970).
23. B. Nilsson and D. Zopf, Arch. Biochem. Biophys., 222, 628-648 (1983).
24. S. B. Svensson and A. A. Lindberg, J. Immunol., 120, 1750-1757 (1978).
25. E. Kallin, H. Lönn, and T. Norberg, Glycoconjugate J., 5, 145-150 (1988).
26. L. M. Likhosherstov, O. S. Novikova, V. A. Derevitskaja, and N. K. Kochetkov, Carbohydr. Res., 146, C1-C5 (1986).
27. B. Paul and W. Korytnyk, Carbohydr. Res., 67, 457-468 (1978).
28. H. S. Isbell and H. L. Frush, J. Org. Chem., 23, 1309-1319 (1958).
29. R. Howe in Rodd's Chemistry of Carbon compounds, Vol. 1C; S. Coffey, Ed.; Elsevier: Amsterdam, 1965, p 290-291.
30. H. Paulsen and K. -W. Pflughaupt in The Carbohydrates, Vol 1B, W. Pigman and D. Horton, Eds.; Academic Press: New York, 1980, p 881-927.
31. J. E. Hodge and B. T. Hofreiter in Methods in Carbohydrate Chemistry, vol 1; R. L. Whistler and M. L. Wolfrom, Eds.; Academic Press: New York, 1962, p 380-394.
32. W. M. Thomas and D. W. Wang in Encyclopedia of Polymer Sience and Engineering, Vol 1, Second Ed.,: Wiley: New York, 1985, p 169-211.
33. S. Sandler and W. Karo, Polymer Synthesis; Vol 1; Academic Press: New york, 1974, p 343-365.
34. Y. Yamazaki and H. Maeda, Agric. Biol. Chem., 45, 2091-2103 (1981).
35. F. Micheel, R. Frier, E. Plate, and A. Hiller, Chem. Ber., 85, 1092-1101 (1952).

TABLE 1

| Conversion of reducing oligosaccharides to the corresponding glycosylamines | |
|---|---|
| Oligosaccharide | Glycosylamine, yield (%) |
| Lactose | 82 |
| Lacto-N-tetraose[a] | 82 |
| Lacto-N-fucopentaose I[b] | 81 |
| Lacto-N-fucopentaose II[c] | 78 |
| Lacto-N-difucohexaose I[d] | 88 |
| 2'-Fucosyllactose | 83 |
| 3'-Siallylactose | 74 |
| A-tetrasaccharide[e] | 88 |
| Cellobiose | 72 |

[a] β-D-Galp-(1→3)-β-D-GlcNAcp-(1→3)-β-D-Galp-(1→4)-D-Glc
[b] α-L-Fucp-(1→2)-β-D-Galp-(1→3)-β-D-GlcNAcp-(1→3)-β-D-Galp-(1→4)D-Glc
[c] β-D-Galp-(1→3)-[α-L-Fucp-(1→4)]-βD-GlcNAcp-(1→3)-β-D-Galp-(1→4)-D-Glc
[d] α-L-Fucp-(1-2)-β-D-Galp-(1→3)-[α-L-Fucp-(1→4)]-β-D-GlcNAcp-(1→3)-β-D-Galp-(1→4)-D-Glc
[e] α-D-GalNAcp-(1→3)-[α-L-Fucp-(1→2)]-β-D-Galp-(1→4)-β-D-Glc
(Nomenclature according to IUPAC-recommendations)

TABLE 2

| Acryloylation of glycosylamines | |
|---|---|
| Glycosylamine | N-acryloylglycosylamine (%) |
| Lactose | 88 |
| Lacto-N-tetraose | 74 |
| Lacto-N-fucopentaose I | 53* |
| Lacto-N-fucopentaose II | 61* |
| 2'-Fucosyllactose | 92 |

TABLE 2-continued

| Acryloylation of glycosylamines | |
|---|---|
| Glycosylamine | N-acryloylglycosylamine (%) |
| A-tetrasaccharide | 65* |

*Yield not optimized

TABLE 3

| Synthesis of copolymers | | | | |
|---|---|---|---|---|
| Oligosaccharide | Yield of copolymer* | Charged ratio** | Polymer ratio | [α]D |
| Lactose | 54 | 1:3 | 1:4,6 | +6 |
| Lacto-N-tetraose | 82 | 1:4 | 1:5 | −1 |
| Lacto-N-fucopentaose I | 59 | 1:4 | 1:6 | −11 |
| A-tetrasaccharide | 48 | 1:6 | 1:14 | +18 |
| 2'-Fucosyllactose | 65 | 1:6 | 1:9 | −30 |

*Yield calculated from starting N-acryloylglycosylamine
**Ratio = ratio N-acryloylglycosylamine/CHCH₂-unit

We claim:
1. A copolymer of an N-acylated monomer and an amide having the general formula:

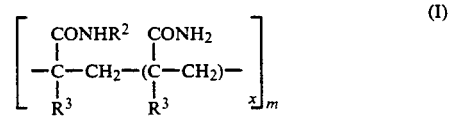

wherein
$R^2$ is a reducing sugar residue;
$R^3$ is H or $CH_3$;
x is an integer from 0 to about 20; and
m is such that the molecular weight of the copolymer is from about 5 kDa to about 2000 kDa.

2. A copolymer according to claim 1, wherein $R^2$ is a mono, di- or oligo-saccharide residue.

3. A copolymer according to claim 2, wherein $R^2$ is the residue of a saccharide having 1 to 10 monosaccharide units.

4. A copolymer according to claim 3, wherein $R^2$ is the residue of a saccharide selected from: lactose, lacto-N-tetraose, lacto-N-fucopentaose I, lacto-N-fucopentaose II, lacto-N-difucohexaose I, 2'-fucosyllactose, 3'-siallyllactose, A-tetrasaccharide, cellobiose.

5. A copolymer according to claim 2 wherein $R^2$ is the residue of a saccharide, having 1 to 6 monosaccharide units.

6. A copolymer according to claim 1, wherein x is from 1 to about 15.

7. A copolymer according to claim 1, wherein m is such that the molecular weight of the copolymer is from about 10 to about 500 KDa.

8. A copolymer according to claim 1, wherein $R^3$ is H.

9. A copolymer of an N-acylated monomer and an amide having the general formula:

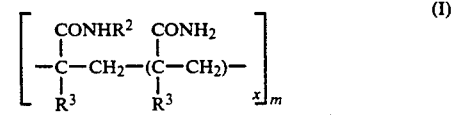

wherein
$R_2$ is a reducing sugar residue which is N-acylated to a meth(acryloyl) at position $C_1$ of the sugar;
$R^3$ is H or $CH_3$;

X is an integer from 0 to about 20 and M is such that the molecular weight of the copolymer is from about 5 kDa to about 2,000 kDa.

10. A copolymer according to claim 9, wherein $R^2$ is a mono, di- or oligosaccharide residue.

11. A copolymer according to claim 10, wherein $R^2$ is the residue of a saccharide having 1 to 10 monosaccharide units.

12. A copolymer according to claim 10, wherein $R^2$ is the residue of a saccharide having 1 to 6 monosaccharide units.

13. A copolymer according to claim 11, wherein $R^2$ is the residue of a saccharide selected from: lactose, lacto-N-tetraose, lacto-N-fucopentaose I, lacto-N-fucopentaose II, lacto-N-difucohexaose I, 2'-fucosyllactose, 3'-siallyllactose, A-tetrasaccharide, cellobiose.

14. A copolymer according to claim 12, wherein $R^2$ is the residue of a saccharide selected from: lactose, lacto-N-tetraose, lacto-N-fucopentaose I, lacto-N-fucopentaose II, lacto-N-difucohexaose I, 2'-fucosyllactose, 3'-siallyllactose, A-tetrasaccharide, cellobiose.

15. A copolymer according to claim 9, wherein X is from 1 to about 15.

16. A copolymer according to claim 9, wherein M is such that the molecular copolymer is from about 10 to about 500 kDa.

17. A copolymer according to claim 9, wherein $R^3$ is H.

* * * * *